United States Patent [19]

Sih

[11] 4,235,788
[45] Nov. 25, 1980

[54] 6,7-DIDEHYDRO- OR 7,8-DIDEHYDRO-PGI$_1$ ACYL-SUBSTITUTED PHENYL ESTERS

[75] Inventor: John C. Sih, Kalamazoo, Mich.

[73] Assignee: The Upjohn Company, Kalamazoo, Mich.

[21] Appl. No.: 48,495

[22] Filed: Jun. 14, 1979

Related U.S. Application Data

[62] Division of Ser. No. 933,329, Aug. 14, 1978, Pat. No. 4,180,657.

[51] Int. Cl.$^3$ .................................... C07D 307/935
[52] U.S. Cl. ........................ 260/346.22; 542/426; 542/429
[58] Field of Search .................. 260/346.22; 542/429, 542/426

[56] References Cited

PUBLICATIONS

Johnson et al., J. Am. Chem. Soc. 99, 4182 (1977).

*Primary Examiner*—Henry R. Jiles
*Attorney, Agent, or Firm*—Robert A. Armitage

[57] ABSTRACT

The present invention relates to novel acyl-substituted esters of 6,7-didehydro- or 7,8-didehydro-PGI$_1$ compounds, e.g., the 4-acetylphenyl ester of such PGI$_1$ analogs. These esters are characterized by pharmacological activity, being for example useful for the pharmacological purposes for which the corresponding free acids are employed.

4 Claims, No Drawings

6,7-DIDEHYDRO- OR 7,8-DIDEHYDRO-PGI$_1$ ACYL-SUBSTITUTED PHENYL ESTERS

The present application is a divisional application of Ser. No. 933,329, filed Aug. 14, 1978, now issued as U.S. Pat. No. 4,180,657, on Dec. 25, 1979.

The present invention relates to prostaglandin analogs for which the essential material constituting a disclosure therefor is incorporated by reference here from U.S. Pat. No. 4,180,657, issued Dec. 25, 1979.

I claim:

1. An acid ester of a prostacyclin analog of the formula

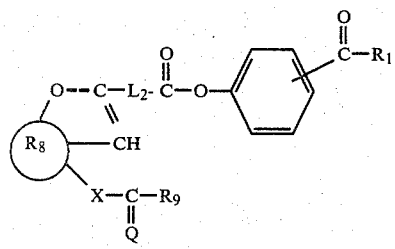

wherein L$_2$ is
  (1) —(CH$_2$)$_n$- wherein n is one to 5 inclusive, or
  (2) —(CH$_2$)$_p$-CF$_2$- wherein p is 2, 3, or 4, wherein Q is

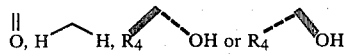

wherein R$_4$ is hydrogen or alkyl of one to 4 carbon atoms, inclusive,
wherein R$_1$ is alkyl of one to 4 carbon atoms, inclusive, with the proviso that when R$_1$ is tert-butyl the

group is in the 4-position, wherein R$_8$ is

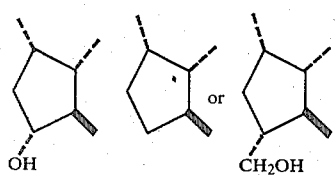

wherein R$_9$ is

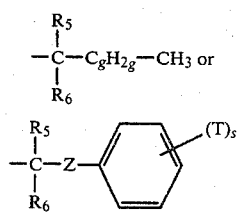

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ where C$_j$H$_{2j}$ is a valence bond or alkylene of one to 9 carbon atoms, inclusive, with one to 6 carbon atoms, inclusive between CR$_5$R$_6$- and the phenyl ring;

wherein T is alkyl of one to 4 carbon atoms, inclusive, fluoro, chloro, trifluoromethyl, or —OR$_7$- wherein R$_7$ is alkyl of one to 4 carbon atoms, inclusive, and s is zero, one, 2 or 3, with the proviso that not more than two T's are other than alkyl and when s is 2 or 3 the T's are either the same or different, and wherein X is
  (1) trans—CH=CH—
  (2) cis—CH=CH—
  (3) —C≡C—or
  (4) —CH$_2$CH$_2$—.

2. Δ$^6$-PGI$_1$, 4-Acetylphenyl ester, a compound according to claim 1.

3. An acid of a prostacyclin analog of the formula

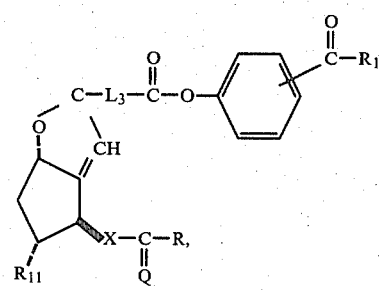

wherein L$_3$ is —(CH$_2$)$_n$-
wherein n is one to 5 and
wherein Q is

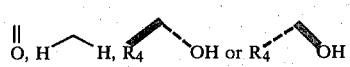

wherein R$_4$ is hydrogen or alkyl of one to 4 carbon atoms, inclusive,
wherein R$_1$ is alkyl of one to 4 carbon atoms, inclusive, with the proviso that when R$_1$ is tert-butyl the

group is in the 4-position, wherein R$_9$ is

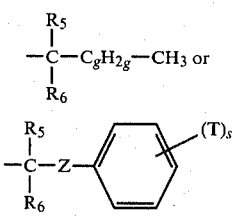

wherein C$_g$H$_{2g}$ is alkylene of one to 9 carbon atoms, inclusive, with one to 5 carbon atoms, inclusive, in the chain between —CR$_5$R$_6$-and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—);
wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms; inclusive, fluoro, chloro, trifluoromethyl, or —$OR_7$—wherein $R_7$ is alkyl of one to 4 carbon atoms, inclusive, and s is zero, one, 2 or 3, with the proviso that not more than two T's are other than alkyl and when s is 2 or 3 the T's are either the same or different,
wherein $R_{11}$ is hydrogen, hydroxy, or hydroxymethyl, and
wherein X is
  (1) trans—CH=CH—
  (2) cis—CH=CH—
  (3) —C≡C— or
  (4) —$CH_2CH_2$—

4. (6R and 6S)-$\Delta^7$-$PGI_1$, 4-Acetylphenyl ester, compounds according to claim 2.

* * * * *

UNITED STATES PATENT OFFICE
CERTIFICATE OF CORRECTION

Patent No. 4,235,788  Dated 25 November 1980

Inventor(s) John C. Sih

It is certified that error appears in the above-identified patent and that said Letters Patent are hereby corrected as shown below:

Column 2, lines 28-35, that portion of the formula reading

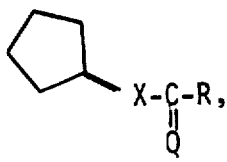 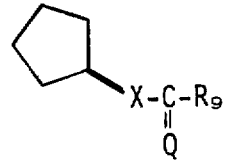

Column 4, line 12, "according to claim 2" should read -- according to claim 3 --.

Signed and Sealed this

Fourteenth Day of April 1981

[SEAL]

Attest:

RENE D. TEGTMEYER

Attesting Officer    Acting Commissioner of Patents and Trademarks